United States Patent
Takasaki

(10) Patent No.: US 6,897,047 B1
(45) Date of Patent: May 24, 2005

(54) HEAT-RESISTANT MANNOSE ISOMERASE, PROCESS FOR PRODUCING THE SAME AND PROCESS FOR PRODUCING MANNOSE BY USING THE SAME

(75) Inventor: Yoshiyuki Takasaki, Chiba (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 09/959,563

(22) PCT Filed: Apr. 21, 2000

(86) PCT No.: PCT/JP00/02630

§ 371 (c)(1),
(2), (4) Date: Mar. 13, 2002

(87) PCT Pub. No.: WO00/66719

PCT Pub. Date: Nov. 9, 2000

(30) Foreign Application Priority Data

Apr. 30, 1999 (JP) .......................... 11/124870

(51) Int. Cl.⁷ .................. C12P 19/24; C12P 19/02; C12N 9/90
(52) U.S. Cl. .................. 435/94; 435/105; 435/233
(58) Field of Search .......................... 435/105, 94, 233

(56) References Cited

U.S. PATENT DOCUMENTS 5,240,717 A * 8/1993 Takasaki et al. ............ 435/233

FOREIGN PATENT DOCUMENTS

| JP | 55-111795 | 8/1980 |
| JP | 4-218370 | 8/1992 |
| JP | 6-292578 | 10/1994 |
| JP | 11-75836 | 3/1999 |

OTHER PUBLICATIONS

Takasaki et al., Journal of Fermentation and Bioengineering, vol. 76, No. 3, pp. 237–239 (1993).

* cited by examiner

*Primary Examiner*—Herbert J. Lilling
(74) *Attorney, Agent, or Firm*—Wenderoth, Lind & Ponack, L.L.P.

(57) ABSTRACT

A thermostable mannose isomerase generated from a bacterium belonging to the genus *Agrobacterium*, excellent in thermostability, capable of being continuously used at a temperature of 55° C. to 60° C. for a prolonged period of time, and has, for example, the following enzymatic properties: (a) function: converts D-mannose to D-fructose and vice versa; (b) substrate specificity: isomerizes the aldoses D-mannose and D-lyxose to their corresponding kitoses, but does not interact with D-glucose, D-galactose, L-mannose, D-xylose, L-xylose, D-arabinose, L-arabinose or D-ribose; (c) optimum pH: 7.5 to 8.5; (d) optimum temperature: 55° C. to 60° C.; and (e) stable pH: 6.0 to 10.0, is provided.

4 Claims, 3 Drawing Sheets

US 6,897,047 B1

HEAT-RESISTANT MANNOSE ISOMERASE, PROCESS FOR PRODUCING THE SAME AND PROCESS FOR PRODUCING MANNOSE BY USING THE SAME

TECHNICAL FIELD

The present invention relates to a novel thermostable mannose isomerase, which may be used for producing mannose, useful as an anti-bacterial substance, food ingredient etc., a method of producing this enzyme, and a method of producing mannose by using the same.

BACKGROUND ART

Mannose has been used as a material for mannitol synthesis and a constituent of animal cell culture medium. Further, it has been shown that mannose inhibits the growth of enterobacteria *Salmonella*, and its use as an additive for drinking water or feed for fowl such as chickens is being considered (R. H. Brown, in Foodstuff, June 12, vol. 10, 1989).

Furthermore, since mannose improves the taste of various types of food, its application as food additive has also been considered.

However, supply of mannose is scarce, since mannose is usually prepared by the acid-hydrolysis of glucomannan contained in plants such as wood and devil's tongue, or by processing glucose under high temperature in the presence of a molybdate catalyst; hence, mannose is extremely expensive.

On the other hand, the inventor of the present application has continued research in hope to establish a technique to produce mannose from fructose produced from glucose, which is in abundance and inexpensive, by using mannose isomerase, which converts mannose to fructose and vice versa, and a technique to produce mannose directly from glucose using mannose isomerase and glucose isomerase (an enzyme which converts D-glucose to fructose and vice versa) in combination.

Mannose isomerase is an enzyme, which was first found in 1956 by Palleroni, Doudoroff et al., in *Pseudomonas saccharophila* (J. Biol. Chem., vol. 218, p. 535, 1956). Later, the inventor of the present application and his coworkers found and reported that a bacterium identified as *Xanthomonas ruburilineans* also produces mannose isomerase (J. Agr. Chem. Soc. Japan, 37, 524, 1963; Agric. Biol. Chem. 28, 601, 1964). Also, the inventor has found and reported that a *Streptomyces bacterium* produces the same enzyme (Report of the Fermentation Research Institute Agency of Industrial Science and Technology, 28, 89, 1966).

However, all of the above conventional mannose isomerases have low optimum temperatures in the range of 35° C. to 40° C., thereby being poor in thermostability and problematic for industrial use.

In relation to this point, the inventor of the present application has invented a thermostable mannose isomerase, which is produced by a *Pseudomonas* bacterium, and filed a Japanese patent application (Japanese Patent Provisional Publication No. 218370/1992).

However, in order to produce mannose from fructose, for example, by using the above-mentioned mannose isomerase as an immobilized enzyme, or to produce mannose from glucose by using glucose isomerase in combination, a mannose isomerase which may be used consistently at a temperature in the range of 55° C. to 60° C. for a prolonged period of time, was required.

The present application addresses the above-described circumstances, and its object is to provide a novel thermostable mannose isomerase that shows excellent stability at high temperature compared to conventional enzymes, and stable under constant use at temperatures in the range of 55° C. to 60° C. for a prolonged period of time.

Further, the present application also provides a method for producing the said thermostable mannose isomerase and a method for producing mannose by using the same.

DISCLOSURE OF INVENTION

As the first invention to solve the above-mentioned problems, the present application provides a thermostable mannose isomerase derived from a bacterium belonging to the genus *Agrobacterium*.

Further, this thermostable isomerase of the first invention has the following enzymatic properties as preferable embodiments:

(a) function: convert D-mannose to D-fructose and vice versa;

(b) substrate specificity: isomerizes the aldoses D-mannose and D-lyxose to their corresponding ketoses, but does not interact with D-glucose, D-galactose, L-mannose, D-xylose, L-xylose, D-arabinose, L-arabinose or D-ribose;

(c) optimum pH: 7.5 to 8.5;

(d) optimum temperature: 55° C. to 60° C.; and (e) stable pH: 6.0 to 10.0.

The present application provides, as the second invention, a method for producing the thermostable mannose isomerase of the above-described first invention, comprising the cultivation of *Agrobacterium* bacteria, and the extraction of the mannose isomerase from the cultivated cell bodies.

The present invention provides, as the third invention, a method for producing mannose, comprising the reaction of fructose with the thermostable mannose isomerase of the above-described first invention, to obtain a mannose-containing liquid from the resultant reaction product.

The present application provides, as the fourth invention, a method for producing mannose, comprising the reaction of glucose with the thermostable mannose isomerase of the above-described first invention and glucose isomerase, to obtain a mannose-containing liquid from the resultant reaction product.

BEST MODE FOR CARRYING OUT THE INVENTION

Figure 1:
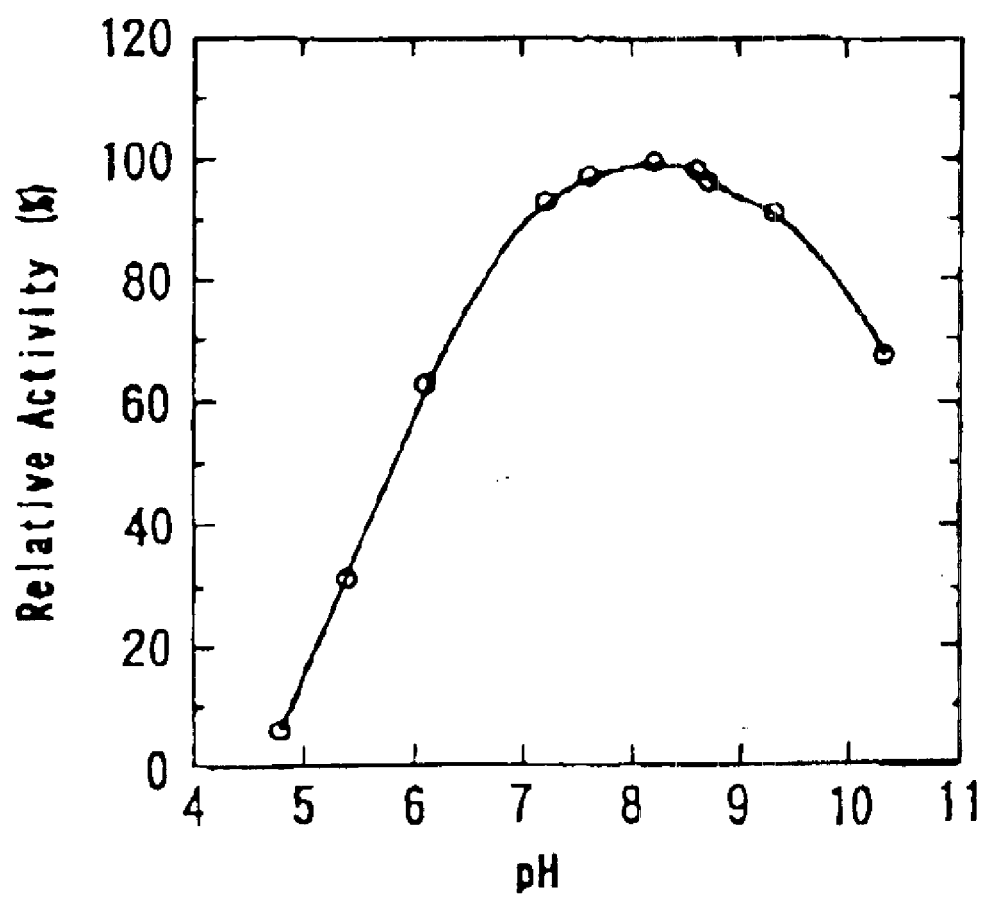
FIG. 1 shows the relationship between the activity of mannose isomerase of the present invention and pH.

The thermostable mannose isomerase of the above-described first invention provided by the present application, as described in the Examples below, is a novel mannose isomerase, which may be used continuously for two to three months at a temperature of 60° C. or for about 10 months at 55° C., thereby showing excellent thermostability. Therefore, in the above-described third and fourth inventions, efficient production of mannose is made possible by using this thermostable mannose isomerase as an immobilized enzyme etc.

Hereinafter, embodiments of the invention are shown to describe the invention of the present application in more detail.

The thermorstable mannose isomerase of the first invention of the present application is an enzyme obtained from a bacterium belonging to the genus Agrobacterium by the method described later (the third invention). The Agrobacterium bacterium is not limited to a specific type, and any known Agrobacterium strain may be used. For example, the inventor of the present application has confirmed that Agrobacterium bacteria such as Agrobacterium tumefaciens (IPO 12664), Agrobacterium rhizogenes (IFO 15196), Agrobacterium sangulneum (IFO 15763), Agrobacterium stellulatum (IFO 15764), Agrobacterium meteori (IFO 15793), and Agrobacterium ruteum (IFO 15768), selected at random from the type culture preserved at the institute of Fermentation Osaka, each produce a thermostable mannose isomerase.

Further, the thermostable mannose isomerase of the first invention may also be obtained from a novel Agrobacterium, which was isolated from soil by the inventor of the present application. The mycological properties of this novel strain are shown in Table 1; through classification by the method of Bergey's Manual of Systematic Bacteriology, Vol. 2 (1986) and Sawada, H., Ieki, H., Oyaizu, H. and Matsumoto, S., Int. J. Syst. Bacteriol, 43, 694–702 (1993), this novel strain was confirmed to be a microorganism of Agrobacterium radiobacter and named Agrobacterium radiobacter MI-1 strain. Further, this MI-1 strain is closely related to Agrobacterium tumefaciens, except that MI-1 has no pathologic property against plants; however, since there were objections against identifying MI-1 as a bacterial strain identical to Agrobacterium tumefaciens, MI-1 was, for the present, identified as Agrobacterium radiobacter. It goes without saying that if both strains come to be unified, its name may be change to one that is appropriate; however, the identity of the bacterium itself will not be influenced.

TABLE 1

| Morphology | |
|---|---|
| Shape of cell: | Rod-shaped bacteria |
| Gram staining: | − |
| Mobility: | + |
| Spore formation: | − |

| Physiological properties | |
|---|---|
| Use of oxygen: | Aerobic |
| Oxydase: | + |
| Catalase: | + |
| OF: | − |
| Pigment of colony: | No specific pigment formation in colony |
| Reduction of nitrate: | + |
| Indole formation: | − |
| Fermentability of glucose: | − |
| Arginine hydrolase: | − |
| Urease: | + |
| Decomposition of esculin: | + |
| Liquefaction of gelatin: | − |
| b-galactosidase: | + |
| Substrate specificity: | D-glucose, L-arebinose, D-mannose, D-mannitol, N-acetylglucosamine, maltose, potassium gluconate, n-capric acid. d,l-malic acid were isomerized: however, adipic acid, sodium citrate and phenyl acetate were not isomerized. |

The thermostable mannose isomerase of the first invention is an enzyme having, for example, the following physicochemical properties:

(A) Function

The isomerase converts D-mannose to D-fructose and vice versa;

(B) Substrate Specificity

The isomerase isomerizes not only D-mannose but also D-lyxose, an aldose, to its corresponding ketose; however, it is not substantially active on such aldoses as D-glucose, D-galactose, L-mannose, D-xylose, L-xylose, D-arabinose, L-arabinose, D-ribose and the like.

(C) Active Ph and Optimum Ph:

When the isomerase acts on a substrate containing 0.1 mol of D-mannose at a temperature of 40° C., the isomerase exerts action at a pH of 4.5 to 11.5. However, the optimum pH is 7.5 to 8.5.

(D) Active Temperature and Optimum Temperature

When the isomerase is allowed to react in the presence of 0.1 mol or D-mannose for 10 minutes, the isomerase exhibits action at temperatures up to about 80° C. However, the optimum temperature is in the range of 55° C. to 60° C.

(E) Stable pH

When the isomerase is left to stand at 25° C. for 3 hours, 90% or more of its potential activity is maintained at a pH in the range of 5.0 to 10.0.

(F) Stable Temperature

When the isomerase is left to stand in a 50 mM tris-HCl buffer of pH 7.5, the iosmerase is stable up to a temperature of about 50° C. and loses about 40% of its activity when heated at 60° C. for 10 minutes.

(G) Inhibition

The isomerase is heavily inhibited by 2 mM of mercury ion, silver ion, copper ion, zinc ion, iron ion, cobalt ion, aluminum ion, p-chloromercurybenzoate, monoiodoacetic acid and the like.

(H) Stabilization

Calcium ion was not effective for protection against deactivation by heat (I) Km (Michaelis Constant)

The Km for D-mannose is about 20 mM (J) Molecular Weight

The molecular weight of the isomerase determined by SDS-PAGE is about 44,000 and that determined by gel filtration is about 95,000; therefore, it is conceived that the isomerase exists as dimers of the same sub-units.

Next, the method for producing the thermostable mannose isomerase of the second invention is described.

When mannose isomerase is produced by cultivating the above-described bacterium belonging to the genus Agrobacterium, an organic nitrogen source used in ordinary microbial cultivation, such as polypeptone, polypeptone S, fish meat extract, corn steep liquor, casein, soybean cake, yeast extract and the like, or an inorganic nitrogen source such as ammonium chloride, ammonium sulfate, urea, ammonium nitrate and the like may be used as nitrogen source.

As the carbon source, various types of sugars such as fructose, glucose, mannose, galactose, an isomerized sugar, sucrose, maltose, xylose, sorbitol, mannitol, dextrin, starch and the like, sugar alcohol, polysaccharide and the like may be used; among these, glucose, fructose, sucrose, galactose, and mannitol are preferable.

In addition to the nitrogen and carbon sources, other substances such as phosphate, magnesium salt and the like may be added.

Cultivation can be carried out at a pH or 5.0 to 9.0 and under a temperature of 25° C. to 40° C. for a period of about one to about 4 days.

Since mannose isomerase is an enzyme produced within a microorganism cell, the enzyme may be directly used by recovering the cells by filtration or centrifugation after cultivation, or used after extraction from the cells by sonication, enzyme (lysozyme), or autolysis. In such cases, the extracted enzyme may optionally be precipitated with ammonium sulfate, acetone, methanol, ethanol and the like and either purified and concentrated, or dried and stored for later use. Further, the extracted enzyme may be purified up to an electrophoretically homogeneous level by ammonium sulfate precipitation at 15% to 50% saturation, DEAE-Sepharose column chromatography, hydroxyapatite adsorption chromatography and the like.

Further, since the *Agrobacterium* cell has mechanical strength and extraction of the enzyme from the cell by autolysis is difficult, for industrial use, the cell, together with a protein, may comprehensively be immobilized by glutaric aldehyde or a combination of chitosan and magnesium carbonate or calcium carbonate, to allow consistent use of the mannose isomerase for a prolonged period of time. Furthermore, after being extracted from the cell body, the mannose isomerase may be immobilized on an appropriate carrier such as DEAE-cellulose and put into use.

Next, the method for producing mannose by the third and fourth inventions is described.

In the method of the third invention, fructose, an isomerized sugar or an invert sugar (sugar derived from hydrolyzing sucrose by an acid or an enzyme (invertase)), which is used as the starting material, is reacted with the thermostable mannose isomerase of the first invention in the presence of 10% to 60% of fructose or a fructose-containing solution at a pH of 6.0 to 9.0 and at a temperature of 50° C. to 60° C. In equilibrium, about 25% of fructose may be converted to mannose. As the source of the invert sugar, inexpensive molasses or blackstrap molasses may also be used.

Further, in the method of the fourth invention, the reaction for producing mannose from glucose using the thermostable mannose isomerase of the present invention and glucose isomerase, may be executed using 10% to 60% of glucose, an isomerized sugar or an invert sugar as the substrate at a pH of 6.0 to 9.0 and at a temperature of 50° C. to 60° C. In this reaction, a sugar mixture composed of about 45% glucose, about 45% fructose and about 10% mannose may be produced.

Furthermore, since the thermostable mannose isomerase of the first invention may convert about 75% of mannose to fructose, the isomerase may be used for converting mannose or a mannose-containing syrup into a syrup having a strong sweetness.

Hereinafter, the invention of the present application is described in more detail showing examples and experiments; however, these embodiments and examples are in no way limiting the present invention.

EXAMPLES

In the examples and experiments shown below, the enzyme activity is measured by the following method:

To 0.5 ml of a 0.1M phosphate buffer (pH 7.0) containing 0.2M mannose, an appropriate amount of the enzyme was added, after which water was added to make the total volume 1.0 ml, and reacted at a temperature of 50° C. After the reaction was terminated by the addition of a 0.5M perchloric acid solution, the amount of fructose produced was determined by the cysteine-carbazole process. The amount of the enzyme, which produces one micromole of fructose in one minute under the above-described conditions is defined as one unit.

Example 1

250 ml of medium (pH 6) containing 2% of polypeptone, 1% of glucose, 0.2% of yeast extract, 0.3% of $K_2HPO_4$, and 0.03% of $MgSO_4.7H_2O$, was put into an Erlenmeyer flask of 1 liter capacity, sterilized in an autoclave at 121° C. for 15 minutes, inoculated with *Agrobacterium tumefaciens* IFO 12664 (ATCC 4718) and subjected to shaking culture at 30° C. for 3 days.

After the cultivation, resultant cells were recovered by centrifugation, rinsed, and parts were disintegrated by an ultrasonic cell disintegrator of 20 KC, followed by the measurement of the activity of the extracted mannose isomerase.

As a result, 0.9 unit of a thermostable mannose isomerase per 1 ml of the cultivation solution was obtained.

Example 2

To test tubes of 18 mm in diameter, 4 ml of media (pH 6.8) each containing 1% of mannose, fructose, glucose, galactose, lactose, maltose or dextrin as the carbon source, 1% of polypeptone, 0.2% of $K_2HPO_4$ and 0.05% of $MgSO_4.7H_2O$ 4 ml, were added, sterilized by conventional methods, and inoculated with *Agrobacterium tumefaciens* IFO 12664, followed by shaking culture at 30° C. for 3 days. After cultivation, the activity of the resultant mannose isomerase was measured as described in Example 1.

Results of the activity measurements are shown in Table 2. Table 2 shows that all of the added carbon sources proved to be effective compared to the medium without any carbon source; the thermostable mannose isomerase of the present invention was therefore confirmed to be an enzyme which may be produced constitutively.

TABLE 2

| Carbon source (1%) | Final pH | Amount of ce (660 nm) | Mannose Isomerase (unit/ml medium) |
|---|---|---|---|
| none | 8.0 | 0.90 | 0.15 |
| mannose | 8.4 | 2.55 | 0.72 |
| fructose | 7.2 | 2.40 | 0.75 |
| gluocose | 8.5 | 2.70 | 0.80 |
| galactose | 8.4 | 2.88 | 0.73 |
| lactose | 8.7 | 2.77 | 0.92 |
| maltose | 8.3 | 2.62 | 0.82 |
| dextrin | 8.8 | 1.92 | 0.52 |

Experiment 1

Using the thermostable mannose isomerase prepared in Example 1, the effect of pH on mannose isomerase reaction was examined.

50 mm each of acetic acid buffer (pH 4.5 to 6.0), tris-HCl buffer (pH 7 to 8.6), glycine-NaOH buffer (pH 8.0 to 10.5) and phosphate buffer ($Na_2HPO_4$—NaOH, pH 8 to 11), 0.1M of mannose and 0.15 units of mannose isomerase were added to form a mixture with a total volume of 0.4 ml, and reacted at 40° C. for 30 minutes. The amount of fructose produced was determined by the cysteine-carbazole process. The relative activities at each pHs are shown in Table 3 and FIG. 1, with the activity at pH 8.2, which was the maximum activity, defined as 100.

TABLE 3

| Reaction pH | Relative Activity (%) |
|---|---|
| 1.8 | 5.6 |
| 5.4 | 31.3 |
| 6.1 | 63.0 |
| 7.2 | 93.4 |
| 7.6 | 97.1 |
| 8.2 | 100.0 |
| 8.6 | 98.3 |
| 8.7 | 96.4 |
| 9.3 | 91.1 |
| 10.3 | 67.7 |
| 11.1 | 9.2 |

Experiment 2

Using the thermostable mannose isomerase prepared in Example 1, the effect of temperature on mannose isomerase reaction was examined.

Figure 2:
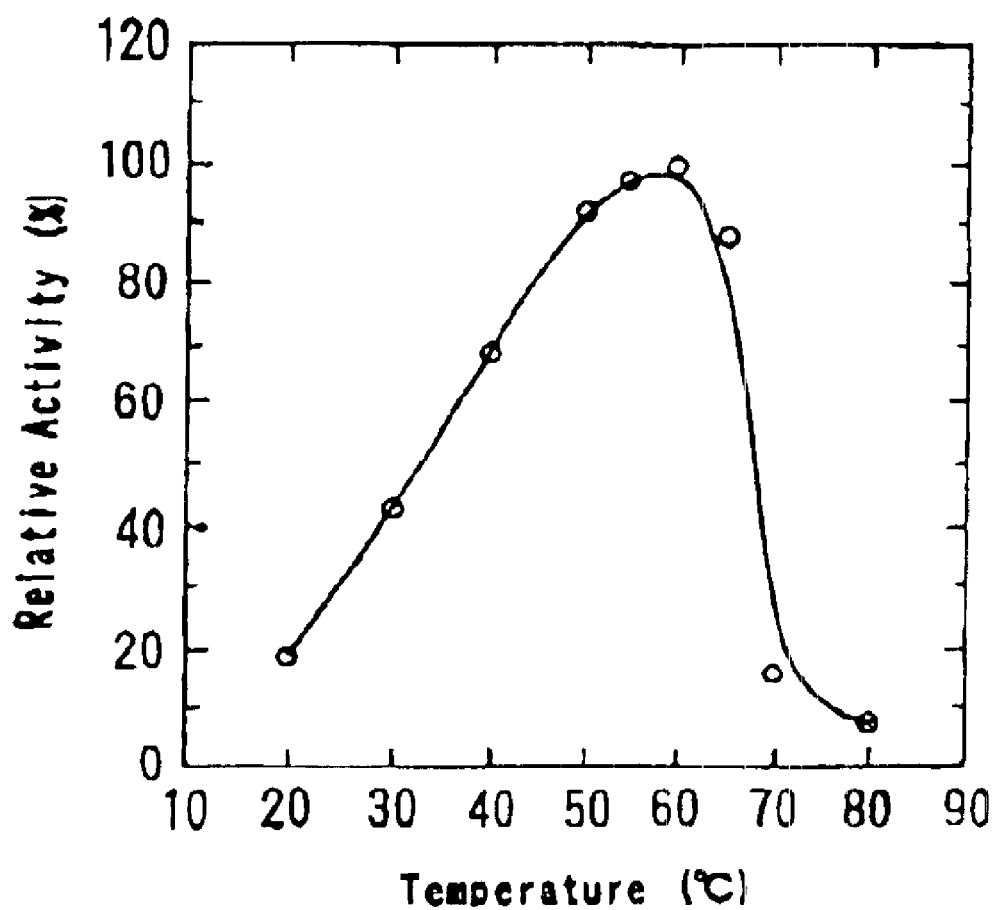
FIG. 2 shows the relationship between the activity of mannose isomerase of the present invention and temperature.

A mixture of 0.1M of mannose, 50 mM of tris-HCl buffer (pH 7.5), and 0.15 unit each of thermostable mannose isomerase with a total volume of 0.4 ml was prepared and subjected to reaction at 20° C. to 80° C. for 10 minutes. The amount of fructose produced was determined by the cysteine-carbazole process. The relative activities at each temperature are shown in Table 2 and FIG. 2 with the activity at 60° C. defined as 100. From these results, the optimum temperature was determined to be in the range of 55° C. to 60° C.

TABLE 4

| Reaction Temperature (° C.) | Relative Activity (%) |
|---|---|
| 20 | 18.7 |
| 30 | 42.5 |
| 40 | 68.9 |
| 50 | 92.1 |
| 55 | 97.1 |
| 60 | 100.0 |
| 65 | 87.9 |
| 70 | 16.5 |
| 80 | 7.0 |

Example 3

Using the thermostable mannose isomerase prepared in Example 1, mannose was produces from fructose.

To 100 mg, 200 mg, 300 mg and 400 mg each of fructose, 50 mM of phosphate buffer (pH 7.0), and 2.2 units of the thermostable mannose isomerase, water was added to form a mixture with a total volume of 1 ml, after which the mixture was subjected to reaction at 50° C. Specific volumes of the reaction mixture were sampled at regular intervals and the amount of the mannose produced was determined by high performance liquid chromatography.

The results are shown in Table 5. As is apparent from Table 5, as the concentration of the substrate becomes higher, the reaction progresses more efficiently and nearly reaches equilibrium in 2 days. In 34 hours, from a fructose concentration of 10%, 20%, 30% and 40%, yields of about 27%, about 23%, about 23% and about 24%, respectively, of mannose were obtained.

TABLE 5

| | Mannose Production Amount (mg/ml) | | | |
|---|---|---|---|---|
| Reaction time | fructose concentrations (mg/ml) | | | |
| (h) | 100 | 200 | 300 | 400 |
| 5 | 17.5 | 26.3 | 35.6 | 46.3 |
| 24 | 25.5 | 42.5 | 64.4 | 92.5 |
| 34 | 26.5 | 43.8 | 67.5 | 95 |

Example 4

1.0 g of chitosan was dissolved in 340 ml of 1.5% acetic acid (weight percent), followed by the addition of 0.25 g of magnesium carbonate and adjustment of pH 1N sodium hydroxide to pH 6.0. To this mixture, a cell suspension of the thermostable mannose isomerase prepared in Example 1 was added drop by drop using a syringe. After 10 minutes at room temperature, the gel obtained was collected and dried at 30° C. The chitosan-immobilized enzyme bacterial cells were packed in a column (D 9 mm×L 70 mm, about 750 units), heated at 55° C. or 60° C. and continuously supplied with a 20% fructose solution (containing 50 mM tris-buffer of pH 7) at a flow rate of about 0.3 ml/minute or 0.5 ml/minute. The amount of mannose produced was determined by high performance liquid chromatography periodically throughout the reaction.

Figure 3:
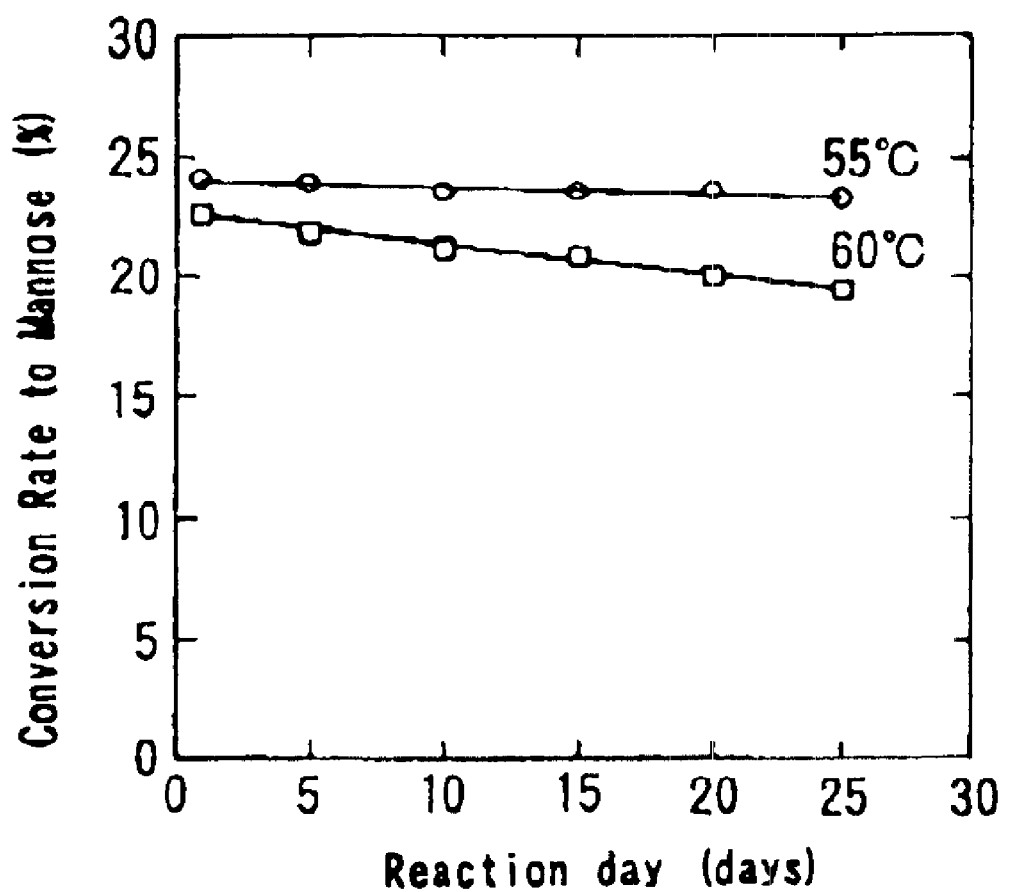
FIG. 3 shows the relationship between the conversion rate from fructose to mannose by the thermostable mannose isomerase of the present invention and the reaction time in days.

The results (conversion amounts from fructose to mannose) are shown in Table 6 and FIG. 3. As is apparent from these results, the immobilized enzyme obtained is stable, and the half-life of enzyme activity (period in which conversion rate becomes half) is about 10 months when reacted at 55° C. and about 2 months to 3 months when reacted at 60° C.

TABLE 6

| | conversion to mannose (%) | |
|---|---|---|
| reaction days | 55° C. | 60° C. |
| 1 | 24 | 22.5 |
| 5 | 23.8 | 21.8 |
| 10 | 23.4 | 21.2 |
| 15 | 23.4 | 20.9 |
| 20 | 23.4 | 20 |
| 25 | 23.1 | 19.4 |

Example 5

To test tubes of 18 mm in diameter, 4 ml of a medium (pH 7.0) containing 1% of polypeptone, 1% of glucose, 0.2% of yeast extract, 0.3% of $K_2HPO_4$ and 0.05% of $MgSO_4.7H_2O$ was added, sterilized in an autoclave at 121° C. for 15 minutes, and inoculated each with *Agrobacterium tumefaciens* IFO-12664 (ATCC 4718), *Agrobacterium tumefaciens* IFO-12665 (ATCC 6466), *Agrobacterium tumefaciens* IFO 13532 (ATCC 19358). *Agrobacterium tumefaciens* IFO 13533 (ATCC 25235). *Agrobacterium radiobacter* MI-1, *Agrobacterium rhizogenes* IFO-15196, *Agrobacterium sangulneum* IFO-15763 (ATCC 25659), *Agrobacterium stellulatum* IFO-15764 (ATCC 15215). *Agrobacterium meteori* IFO-15793 and *Agrobacterium luteum* IFO-15768 (ATCC 25657), and subjected to Shaking culture at 30° C. for 3 days. After cultivation, the cell bodies were recovered by centrifugation, rinsed and disrupted by an ultrasonic cell disintegrator of 20 KC, and the activity of the extracted mannose isomerase was measured.

The production amount of mannose isomerase in each of the above-described media is shown in Table 7; the thermos table mannose isomerase was obtained by any of the above-described bacteria of the genus *Agrobacterium*.

TABLE 7

| *Agrobacterium* strain | Mannose Isomerase Production (unit/ml medium) |
| --- | --- |
| *Agrobacterium tumefaciens* IFO12665 | 0.374 |
| *Agrobacterium tumefaciens* IFO13532 | 0.313 |
| *Agrobacterium tumefaciens* IFO13533 | 0.346 |
| *Agrobacterium radiobacter* M1-1 MI-1 | 1.501 |
| *Agrobacterium rhizogenes* IFO15196 | 0.042 |
| *Agrobacterium sangulneum* IFO15763 | 0.094 |
| *Agrobacterium stellulatum* IFO15764 | 0.100 |
| *Agrobacterium meteori* IFO15793 | 0.104 |
| *Agrabacterium luteum* IFO15768 | 0.104 |

Experiment 3

The enzymatic properties of mannose isomerase derived from strains (1) to (9) of Table 7, obtained in Example 5 were examined.

Results are shown in Table 8; the mannose isomerase derived from strains (1) to (9) were all extremely similar to the thermostable mannose isomerase obtained in Example 1, and showed optimum pH in the range of 7.5 to 8.5, optimum temperature in the range of 55° C. to 60° C., stable pH in the range of 6 to 10 and a stable temperature in the range of 50° C. to 60° C.

TABLE 8

| Strain | Optimun temperature (° C.) | Optimum pH | Stable pH | Stable Temperature (° C.) |
| --- | --- | --- | --- | --- |
| (1) | about 55 | 7.7 | 6–10 | 50–60 |
| (2) | about 55 | 8.0 | 6–10 | 50–60 |
| (3) | about 55 | 8.1 | 6–10 | 50–60 |
| (4) | about 60 | 8.0 | 6–10 | 50–60 |
| (5) | about 55 | 7.8 | 6–10 | 50–60 |
| (6) | about 60 | 8.2 | 6–10 | 50–60 |
| (7) | about 60 | 7.5 | 6–10 | 50–60 |
| (8) | about 55 | 8.5 | 6–10 | 50–60 |
| (9) | about 55 | 8.1 | 6–10 | 50–60 |

Industrial Applicability

As described above in detail, the present application provides a thermostable mannose isomerase originating from *Agrobacterium* bacteria, which is excellent in thermo-stability and usable continuously at a temperature range of 55° C. to 60° C. for a prolonged period of time. By this finding, the efficient production of mannose, which is useful as anti-bacterial substance or food material, is made possible.

What is claimed is:

1. A thermostable mannose isomerase, which is generated from a bacterium belonging to the genus *Agrobacterium*, which thermostable mannose isomerase shows the following enzymatic properties:
    (a) function: converts D-mannose to D-fructose and vice versa;
    (b) substrate specificity: isomerizes the aldoses D-mannose and D-lyxose to their corresponding ketoses; however, does not function with D-glucose, D-galactose, L-mannose, D-xylose, L-xylose, D-arabinose, L-arabinose or D-ribose;
    (c) optimum pH: 7.5 to 8.5;
    (d) optimum temperature: continuously for two to three months at a temperature of 60° C.; and
    (e) stable pH: 6.0 to 10.0.

2. A method for producing the thermostable mannose isomerase of claim 1, comprising:
    the cultivation of a bacterium belonging to the genus *Agrobacterium*; and
    the extraction of the mannose isomerase from the bacterial cell bodies.

3. A method for producing mannose comprising:
    the reaction of fructose with the thermostable mannose isomerase of claim 1; and
    obtaining a mannose-containing liquid from the resultant reaction product.

4. A method for producing mannose comprising:
    the reaction of glucose with the thermostable mannose isomerase of claim 1 and glucose isomerase; and
    obtaining a mannose-containing liquid from the resultant reaction product.

* * * * *